United States Patent
Lee et al.

(10) Patent No.: US 10,322,158 B2
(45) Date of Patent: *Jun. 18, 2019

(54) METHOD OF TREATMENT OF INSULIN-RESISTANCE DIABETES MELLITUS

(71) Applicant: Chen-Yu Lee, Taipei (TW)

(72) Inventors: Chen-Yu Lee, Taipei (TW); Yan-Chih Liao, Taipei (TW)

(73) Assignee: Chen-Yu Lee, Taipei (TW)

( * ) Notice: Subject to any disclaimer, the term of this patent is extended or adjusted under 35 U.S.C. 154(b) by 18 days.

This patent is subject to a terminal disclaimer.

(21) Appl. No.: 15/642,578

(22) Filed: Jul. 6, 2017

(65) Prior Publication Data

US 2019/0008917 A1  Jan. 10, 2019

(51) Int. Cl.

| | |
|---|---|
| *A61K 35/618* | (2015.01) |
| *A61K 36/8945* | (2006.01) |
| *A61K 35/32* | (2015.01) |
| *A61K 33/26* | (2006.01) |
| *A61K 36/21* | (2006.01) |
| *A61K 36/65* | (2006.01) |
| *A61K 36/64* | (2006.01) |
| *A61K 36/14* | (2006.01) |
| *A61K 36/258* | (2006.01) |
| *A61K 36/718* | (2006.01) |
| *A61K 36/605* | (2006.01) |
| *A61K 36/126* | (2006.01) |
| *A61K 36/236* | (2006.01) |
| *A61K 36/537* | (2006.01) |
| *A61K 36/734* | (2006.01) |
| *A61K 36/232* | (2006.01) |
| *A61K 36/488* | (2006.01) |
| *A61K 36/756* | (2006.01) |
| *A61K 33/06* | (2006.01) |
| *A61K 36/8988* | (2006.01) |
| *A61K 36/88* | (2006.01) |
| *A61K 36/35* | (2006.01) |
| *A61K 36/61* | (2006.01) |
| *A61K 36/284* | (2006.01) |
| *A61K 36/884* | (2006.01) |
| *A61K 36/17* | (2006.01) |
| *A61K 36/804* | (2006.01) |

(52) U.S. Cl.
CPC .......... *A61K 36/8945* (2013.01); *A61K 33/06* (2013.01); *A61K 33/26* (2013.01); *A61K 35/32* (2013.01); *A61K 35/618* (2013.01); *A61K 36/126* (2013.01); *A61K 36/14* (2013.01); *A61K 36/17* (2013.01); *A61K 36/21* (2013.01); *A61K 36/232* (2013.01); *A61K 36/236* (2013.01); *A61K 36/258* (2013.01); *A61K 36/284* (2013.01); *A61K 36/35* (2013.01); *A61K 36/488* (2013.01); *A61K 36/537* (2013.01); *A61K 36/605* (2013.01); *A61K 36/61* (2013.01); *A61K 36/64* (2013.01); *A61K 36/65* (2013.01); *A61K 36/718* (2013.01); *A61K 36/734* (2013.01); *A61K 36/756* (2013.01); *A61K 36/804* (2013.01); *A61K 36/88* (2013.01); *A61K 36/884* (2013.01); *A61K 36/8988* (2013.01)

(58) Field of Classification Search
None
See application file for complete search history.

(56) References Cited

U.S. PATENT DOCUMENTS

| | | | | |
|---|---|---|---|---|
| 6,093,403 | A * | 7/2000 | Huo | A61K 36/00 424/195.15 |
| 10,149,883 | B1 * | 12/2018 | Lee | A61K 36/9068 |
| 2015/0238542 | A1 * | 8/2015 | Kim | A61K 35/618 424/547 |
| 2017/0197891 | A1 * | 7/2017 | Huang | C05G 3/02 |

OTHER PUBLICATIONS

Chen-Yu Lee et al., "Integrated TCM and Western Medicine Efficacy in the Treatment of Diabetic Encephalopathy", Dec. 2016, vol. 4, No. 1, pp. 9-33.

* cited by examiner

*Primary Examiner* — Ralph J Gitomer
(74) *Attorney, Agent, or Firm* — Bacon & Thomas, PLLC

(57) ABSTRACT

A therapeutic method of treatment of diabetes mellitus, particularly diabetes which acquires insulin resistance, including administering a therapeutically effective amount of Chinese herbal medicine to a subject in need. The Chinese herbal medicine is the decocting extract including the mixture of raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmannia*), and semen Platycladi (*Platycladi Semen*).

9 Claims, No Drawings

METHOD OF TREATMENT OF INSULIN-RESISTANCE DIABETES MELLITUS

BACKGROUND OF THE INVENTION

1. Field of the Invention

The present invention is directed to a method of treatment of diabetes mellitus; in particular, to a method of treatment of insulin-resistance diabetes mellitus.

2. Description of Related Art

The application of Chinese herbal medicine in treatment of cancer attracts significant attentions for a long time. In recent years, the Chinese herbal medicine is also gradually applied to treatment of some metabolic diseases, too.

Diabetes mellitus (or diabetes) is a metabolic disease, whose typical symptoms include high blood sugar levels over a prolonged period, and being difficult to maintain the normal value. Other diabetic syndromes and complications include but are not limited to polyphagia, polydipsia, polyuria, blurry vision, headache, fatigue, slow healing of wound, cardiovascular disease, stroke, chronic renal disease, foot ulcer, and retinopathy.

In present time, there is no effective medicine to cure diabetes but the general treatment simply ameliorates the conditions, including administration of hypoglycemic drug, improving diet, lifestyle, and weight loss. Regular diabetes drugs include Biguanides, Thiazolidinediones, Sulfonylureas, and Glycosurics. The effect of these medicines comprises improving sensitivity to insulin, increasing the amount of secretion of insulin, or increasing the excretion of sugar.

Diabetes patients who are administered insulin for a long period are prone to acquire insulin-resistance, which causes that the dosage would be increased in order to achieve the equal effect. However, overdose of insulin might result in adverse effects, e.g. hypoglycemia, hypokalemia, lipoatrophy, refractive error or blurry vision, etc. Therefore, it is necessary to develop a new diabetes drug that can recover insulin effect, alleviate diabetic symptoms, and avoid withdrawal symptoms.

SUMMARY OF THE INVENTION

One of the objects of the present application is to provide a method of the treatment of diabetes mellitus.

Another objective of the present application is to provide a method of treatment of insulin-resistance diabetes mellitus.

The method of treatment of insulin-resistance diabetes mellitus, comprising administering a therapeutically effective amount of a Chinese herbal medicine to a subject in need;

wherein the Chinese herbal medicine is an extract of a first mixture comprising raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmanniae Radix* or *Rehmannia*), and semen Platycladi (*Platycladi Semen*).

In a preferred embodiment of the present invention, the preparation of the Chinese herbal medicine comprises following steps: providing the first mixture; mixing the first mixture and water to form a second mixture; heating the second mixture to obtain a crude extract; and filtering the crude extract and retaining the liquid, to obtain the Chinese herbal medicine.

In a preferred embodiment of the present invention, wherein the Chinese herbal medicine is the extract of the first mixture comprising 4-6 parts by weight of raw oyster shell powder, 4-6 parts by weight of raw Os Draconis, 7-9 parts by weight of Haematitum (Hematite), 2-4 parts by weight of Magnetitum (Magnetite), 4-6 parts by weight of radix Achyranthis Bidentatae (*Achyranthes bidentata*), 4-6 parts by weight of rhizoma Dioscoreae (*Dioscoreae Rhizoma*), 4-6 parts by weight of radix Paeoniae Rubra (*Paeoniae Radix Rubra*), 4-6 parts by weight of radix Rehmanniae (*Rehmanniae Radix* or *Rehmannia*), and 3-5 parts by weight of semen Platycladi (*Platycladi Semen*).

In a preferred embodiment of the present invention, wherein the part by weight of the first mixture is 3.75 gram per part.

In a preferred embodiment of the present invention, wherein the first mixture further comprises Radix Ginseng (*Ginseng Radix et Rhizoma*), Radix Panax notoginseng (*Notoginseng Radix et Rhizoma*), 5-25 parts by weight of rhizoma Coptidis (*Coptidis Rhizoma*), 5-20 parts by weight of cortex Mori (*Mori Cortex*), 7-9 parts by weight of rhizoma Drynariae (*Drynariae Rhizoma*), 3-5 parts by weight of Rhizoma Chuanxiong (*Chuanxiong Rhizoma*), 3-5 parts by weight of Radix Salviae Miltiorrhizae (*Salviae Miltiorrhizae Radix et Rhizoma*), 3-5 parts by weight of Fructus Crataegi (*Crataegi Fructus*), 2-4 parts by weight of Radix Angelicae Sinensis (*Angelicae Sinensis Radix*), 4-6 parts by weight of Radix Pueraria (*Puerariae Lobatae Radix*), 10-17 parts by weight of Phelloendron amurense bark (*Phellodendri Chinensis Cortex*), 8-12 parts by weight of gypsum powder, 3-5 parts by weight of rhizoma Gastrodiae (*Gastrodiae Rhizoma*), 3-5 parts by weight of Radix asparagi (*Asparagi Radix*), 7-9 parts by weight of Radix Dipsaci (*Dipsaci Radix*), 0-3 parts by weight of salt, 2-4 parts by weight of Pimenta officinalis seed, 2-4 parts by weight of Atractylodes Lancea Rhizoma (*Atractylodis Rhizoma*), 0-3 parts by weight of velvet antler, 4-6 parts by weight of Alisma rhizome (*Alismatis Rhizoma*), 0-3 parts by weight of Herba Ephedrae (*Ephedrae Herba*), or the combination thereof.

In a preferred embodiment of the present invention, wherein the method further comprises administering a therapeutically effective amount of insulin or the analog thereof to a subject in need.

In a preferred embodiment of the present invention, wherein the treatment of the insulin-resistance diabetes mellitus is the treatment of hyperglycemia.

In a preferred embodiment of the present invention, wherein the diabetes mellitus is familial hereditary diabetes.

In a preferred embodiment of the present invention, wherein the extract or powder of the Chinese herbal medicine is administered via oral administration, enteral administration, or intravenous injection.

In a preferred embodiment of the present invention, wherein the Chinese herbal medicine further comprises pharmaceutically acceptable carrier, stabilizer, diluent, dispersant, suspending agents, thickening agent, or excipient, or the combination of the said.

Another objective of the present invention provides a method of reducing the dosage of insulin of diabetes subject, comprising administering a therapeutically effective amount of Chinese herbal medicine to a subject in need;

wherein the Chinese herbal medicine is an extract of a first mixture comprising raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmanniae Radix* or *Rehmannia*), and semen Platycladi (*Platycladi Semen*).

DETAILED DESCRIPTION OF THE PREFERRED EMBODIMENT

The features of the present invention are set forth with particularity in the appended claims. A better understanding of the features and advantage thereof will be demonstrated by reference to the following detailed description that sets forth illustrative embodiments, in which the principles of the invention are employed.

Certain Pharmaceutical and Medical Terminology

Unless otherwise specified, the following terms used in the specification and claims have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology can be employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described. Unless otherwise indicated, all materials employed in the present invention are available in the ordinary markets.

The term "diabetes" or "diabetes mellitus", as used herein, refers to type 1 diabetes, type 2 diabetes, gestational diabetes, or diseases and conditions having typical signs or symptoms of diabetes mellitus.

The term "carrier" or "excipient", as used herein, refers to relatively nontoxic chemical compounds or agents that facilitate the incorporation of a compound into cells or tissues without interfering the effect of the treatment.

The term "diluent", as used herein, refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The aforementioned vehicles can further comprise aromatics, buffering agents, binders, colorants, disintegrants, emulsifiers, extenders, flavor-improving agents, gellants, glidants, preservatives, skin-penetration enhancers, solubilizers, stabilizers, dispersing agents, suspending agents, sweeteners, tonicity agents, viscosity-increasing agents, or the combination thereof.

The term "pharmaceutically acceptable", as used herein, refers to the compounds, formulations, composition, and/or dose form, within the scope of reasonable medical judgment, suitable for contacting with the suffered subject, without undue detrimental effect, toxicity, irritation, allergic response, or any conditions or complications on the general health of the subject being treated, and commensurate with a reasonable benefit/risk ratio.

The term "effective amount" or "therapeutically effective amount", as used herein, refers to a sufficient amount of an agent or a compound being administered which will relieve one or more of the symptoms of the disease or condition being treated to some extent; the result thereof can be reduction and/or alleviation of the signs, symptoms, or causes of a disease, or any other desired alteration of a biological system. For example, an "effective amount" for therapeutic uses is the amount of the composition as disclosed herein required to provide a clinically significant decrease in disease symptoms. An appropriate "effective" amount in any individual case may be determined using techniques, such as a dose escalation study.

The term "enhance", "enhancing", or the like, as used herein, means to increase or prolong either in potency or duration of a desired effect. Thus, in regard to enhancing the effect of therapeutic agents, the term "enhancing" refers to the ability to increase or prolong, either in potency or duration, the effect of other therapeutic agents on a system.

The term "treat," "treating", "treatment", or the like, as used herein, includes alleviating, abating or ameliorating at least one symptom of a disease or condition, preventing disease progression, inhibiting the disease or condition, e.g., arresting the development of the disease or condition, relieving the disease or condition, causing regression of the disease or condition, relieving the condition caused by the disease or condition, or reducing the sign or symptoms of the disease or condition either prophylactically and/or therapeutically.

The term "resistance" or the like, as used herein, refers to the regression of the sensitivity to certain medicine, increment of therapeutically effective amount compared to the expected effect, after a series of course of treatment are taken by a subject in need. The term "drug-resistance" or the like, as used herein, is resistance to a single drug or multidrug resistance.

The term "tolerance", as used herein, refers to the adaptive reaction or reduced reaction of cell, tissue, organisms to the drug after a series of course of treatment are taken by a subject in need, and leading to symptoms of withdrawal upon abruption or decrease in intake of medicine.

General Consideration for Combination Treatments

The term "combination therapy" or the like, as used herein, refers to giving or administering to a suffered subject at least two selected pharmaceuticals, further comprising a course of treatment, via the same or different routes simultaneously, concurrently or sequentially.

In general, the medicines or compositions described herein and, in embodiments where combinational therapy is employed based on the mode of action described herein, other agents do not have to be administered in the same pharmaceutical composition; and in some embodiments, because of different physical and chemical characteristics, they are administered by different routes. In some embodiments, the initial administration is made according to established protocols, and then, based upon the observed effects, the dosage, modes of administration and times of administration is modified by the skilled clinician.

In the embodiment herein, therapeutically-effective dosages vary when the drugs are used in treatment combinations. Combination treatment further includes periodic treatments that start and stop at various times to assist with the clinical management of the patient. For combination therapies described herein, dosages of the co-administered compounds vary depending on the type of co-drug employed, on the specific drug employed, on the disease, disorder, or condition being treated and so forth. The term "combination" or the like, as used herein, means a product that results from combining more than one active pharmaceutical and includes both fixed and non-fixed combinations of the active ingredients. The term "fixed combination" means that the active pharmaceuticals are administered to a patient simultaneously in the form of a single entity or dosage. The term "non-fixed combination" means that the active pharmaceuticals are administered to a patient as separate entities either simultaneously, concurrently or sequentially with no specific intervening time limits, wherein such administration provides effective levels of the pharmaceuticals in the body of the patient. The latter may also be applied to cocktail therapy, e.g. the administration of three or more active ingredients.

The dose forms of the Chinese herbal medicine provided in the present invention include but are not limit to solution, emulsion, suspension, powder, tablet, pill, lozenge, troche, chewing gum, capsule, or any dose form which is suitable for the Chinese herbal medicine provided herein.

The present invention provides a method of treatment of insulin-resistance diabetes mellitus, comprising administering a therapeutically effective amount of Chinese herbal medicine to a subject in need, wherein the Chinese herbal medicine is an extract of a first mixture comprising raw oyster shell powder, raw Os Draconis, Haematitum (Hematite), Magnetitum (Magnetite), radix Achyranthis Bidentatae (*Achyranthes bidentata*), rhizoma Dioscoreae (*Dioscoreae Rhizoma*), radix Paeoniae Rubra (*Paeoniae Radix Rubra*), radix Rehmanniae (*Rehmanniae Radix* or *Rehmannia*), and semen Platycladi (*Platycladi Semen*).

The present invention additionally provides a method of reducing the dosage of insulin for a diabetes subject, comprising administering the therapeutically effective amount of aforementioned Chinese herbal medicine to a subject in need. The said method is directed to reduce the minimal effective dose of insulin which is needed by a diabetes patient.

In an embodiment, the Chinese herbal medicine can be co-administered with another pharmaceutical composition according to the method of treatment of drug-resistance diabetes mellitus. In a specific embodiment, the Chinese herbal medicine and another pharmaceutical composition are administered simultaneously, concurrently or sequentially.

In an embodiment of the present invention, the pharmaceutical composition said above comprises the pharmaceuticals for treating diabetes disclosed in the prior art, which include, but are not limited to, insulin and the modifiers thereof; biguanide such as metformin, pheformin, and buformin; thiazolidinediones such as rosiglitazone, pioglitazone, and troglitazone; sulfonylurea such as glimepiride, glyburide, glipizide, glipizide, chloropropamide, and tolbutamide; meglitinides such as repaglinide, nateglinide; α-glucosidase inhibitors such as miglitol, acarbose, and voglibose; HMG CoA reductase inhibitor such as mevastatin, lovastatin, simvastatin, atorvastatin, and pitavastatin; SGLT2 inhibitor such as Dapagliflozin, Empagliflozin, Canagliflozin, Ipragliflozin, and Tofogliflozin; DPP-4 inhibitors such as sitagliptin, vildagliptin, saxagliptin, linagliptin, dutogliptin, gemigliptin, alogliptin, and teneligliptin.

The method according to the present invention is the treatment of diabetes mellitus and the complications, syndromes, metabolic disorder, or conditions, including but not limited to type 1 diabetes, type 2 diabetes, gestational diabetes, beta cell genetic deficiency, diabetic ketoacidosis, atherosclerosis, cardiovascular diseases, high blood sugar, hypertension, hyperlipidemia, obesity, acute or chronic renal failure, retinopathy, diabetic foot ulcer, insulin resistance, albuminuria, hyperuricemia, swollen, decreased glucose tolerance. In particular, the method is the treatment of drug-resistance diabetes mellitus.

The foregoing scopes are merely suggestive, as the number of variables in regard to an individual treatment regime is large, and considerable excursions from these recommended values are not uncommon. Such dosages, indication, administration, and intake may be altered depending on a number of variables, not limited to the activity of the compound used, the disease or condition to be treated, the mode of administration, the requirements of the individual subject, the severity of the disease or condition being treated, and the judgment of the practitioner.

Preparation of the herbal material and the Chinese herbal medicine.

The present invention is directed to an use of Chinese herbal medicine which includes the extract of a first mixture that mixes the following components: 5 parts by weight of raw oyster shell powder, 5 parts by weight of raw long gu (Os Draconis) powder, 8 parts by weight of Haematitum (Hematite) powder, 3 parts by weight of Magnetitum (Magnetite) powder, 5 parts by weight of radix Achyranthis Bidentatae (*Achyranthes bidentata*), 5 parts by weight of rhizoma Dioscoreae (Dioscorea opposita or *Dioscoreae Rhizoma*), 5 parts by weight of radix Paeoniae Rubra (*Paeoniae Radix Rubra*), 5 parts by weight of radix Rehmanniae (Rehmannia glutinosa, *Rehmanniae Radix*, or *Rehmannia*), and 4 parts by weight of semen Platycladi (Platycladus orientalis or *Platycladi Semen*); wherein it is a daily dose of the Chinese herbal medicine when the part by weight of the first mixture is 3.75 g per part.

In addition, the first mixture can optionally include at least one of the following components or the combination of at least two thereof:

Radix Ginseng (Panax Ginseng or *Ginseng Radix et Rhizoma*), Radix *Panax notoginseng* (*Notoginseng Radix et Rhizoma*), 5-25 parts by weight of rhizoma Coptidis (Coptis chinensis, C. deltoidea, C. teeta, or *Coptidis Rhizoma*), 5-20 parts by weight of cortex Mori (Morus alba or *Mori Cortex*), 7-9 parts by weight of rhizoma Drynariae (Drynaria fortunei or *Drynariae Rhizoma*), 3-5 parts by weight of Rhizoma Chuanxiong (Ligusticum chuanxiong or *Chuanxiong Rhizoma*), 3-5 parts by weight of Radix Salviae Miltiorrhizae (*Salviae Miltiorrhizae Radix et Rhizoma*), 3-5 parts by weight of Fructus Crataegi (Crataegus pinnatifida or *Crataegi Fructus*), 2-4 parts by weight of Radix Angelicae Sinensis (*Angelicae Sinensis Radix*), 4-6 parts by weight of Radix Puerariae (Pueraria Lobata or *Puerariae Lobatae Radix*), 10-17 parts by weight of Phelloendron amurense bark (*Phellodendri Chinensis Cortex*), 8-12 parts by weight of gypsum ($CaSO_4.2H_2O$) powder, 3-5 parts by weight of rhizoma Gastrodiae (Gastrodia elata or *Gastrodiae Rhizoma*), 3-5 parts by weight of Radix asparagi (Asparagus cochinchinensis or *Asparagi Radix*), 7-9 parts by weight of Radix Dipsaci (Dipsacus asperoides or *Dipsaci Radix*), 0-3 parts by weight of salt, 2-4 parts by weight of Pimenta officinalis seed, 2-4 parts by weight of *Atractylodes Lancea Rhizoma* (*Atractylodis Rhizoma*), 0-3 parts by weight of Velvet antler, 4-6 parts by weight of *Alisma* rhizome (Alisma orientalis or *Alismatis Rhizoma*), or 0-3 parts by weight of Herba Ephedrae (Ephedra sinica, E. equisetina, E. intermedia, or *Ephedrae Herba*).

The preparation method of the Chinese herbal medicine is provided as following.

The components of the first mixture are heated and extracted in a solvent; wherein the component of the first mixture can be optionally grinded before extraction to achieve the best extraction outcome, except that raw long gu powder, Haematitum (Hematite) powder, and Magnetitum (Magnetite) powder should be extracted in powder. The preferred solvent of the extraction is water, ethanol, DMSO (Dimethyl sulfoxide), or the combination thereof.

In a preferred embodiment of the present invention, the components of the daily dose of the Chinese herbal medicine are dissolved in 1,600 ml water to obtain a second mixture; the second mixture is decocted at 100-120° C. for 1 hour and then the residue of decoction is filtered out to obtain the liquid extract. Preferably, the liquid extract is equally divided into 3 doses for ter in die administration. Preferably, the second mixture is decocted at 100-120° C. for 1 hour and then the volume of the liquid extract after filtration is 450 ml.

Furthermore, the preparation method of the Chinese herbal medicine can include the step of concentration as follows: after the residue of the extract is filtered out, the liquid extract is condensed by vacuum or low pressure concentration under the condition of 50-60° C. and 20-40 torr, in order to obtain the condensate; preferably, the volume of the condensate is ⅒-1/20 volume of the liquid extract.

Furthermore, the corn starch used as an excipient is added to the condensate to obtain herbal paste; wherein the quantity of the corn starch depends on the stability of condensate; wherein the paste is optionally subject to granulation by spray-drying method.

Example 1 Patient 1

The diabetes patient of example 1 was diagnosed to have the condition including GLU(AC):102, administering insulin approximately 79 U for one day for at least 6 years to improve diabetic symptoms, and diabetic retinopathy.

The treatment for the patient in example 1 comprised: daily administration of the daily dose of the Chinese herbal medicine according to the present invention for a period of 7 consecutive days; specifically, a daily dose of Chinese herbal medicine was equally divided for ter in die administration.

After the 7 days course of treatment (administering daily dose for each day), the outcome of the condition of the diabetes patient included:

GLU(AC) reduced to 79-93 approximately; during the course of treatment, 73 U of insulin was needed for one day. The Chinese herbal medicine of the present invention was able to substitute insulin and achieve the purpose of alleviating diabetic condition as well as abstaining drug dependence without suffering from withdrawal symptoms.

Example 2: Patient 2

The diabetes patient of example 2 was diagnosed to have the condition including GLU(AC): 177-180, administering insulin approximately 66 U for one day for years to improve diabetic symptoms, and diabetic retinopathy.

The treatment for the patient in example 2 comprised: daily administration of the daily dose of the Chinese herbal medicine according to the present invention for a period of 7 consecutive days; specifically, a daily dose of Chinese herbal medicine was equally divided for ter in die administration. Particularly, the daily dose of the Chinese herbal medicine in example 2 was the extract of the first mixture; wherein the first mixture additionally included 18 parts by weight of rhizoma Coptidis (*Coptidis Rhizoma*), 18 parts by weight of cortex Mori (*Mori Cortex*), 4 parts by weight of Rhizoma Chuanxiong (*Chuanxiong Rhizoma*), 8 parts by weight of rhizoma Drynariae (*Drynariae Rhizoma*), 4 parts by weight of Radix Salviae Miltiorrhizae (*Salviae Miltiorrhizae Radix* et *Rhizoma*), 4 parts by weight of Fructus Crataegi (*Crataegi Fructus*), 3 parts by weight of Radix Angelicae Sinensis (*Angelicae Sinensis Radix*), 3 parts by weight of Radix Ginseng (*Ginseng Radix* et *Rhizoma*), and 3 parts by weight of Radix Panax notoginseng (*Notoginseng Radix* et *Rhizoma*).

After the 7 days course of treatment (administering daily dose for each day), the outcome of the condition of the diabetes patient included:

GLU(AC) reduced to 93-136 approximately; during the course of treatment, 58 U of insulin was needed for one day. The Chinese herbal medicine of the present invention was able to substitute insulin and achieve the purpose of alleviating diabetic condition as well as abstaining drug dependence without suffering from withdrawal symptoms.

Example 3: Patient 3

The diabetes patient of example 3 was diagnosed to have the condition including GLU(AC):150, administering insulin approximately 46 U for one day for years to improve diabetic symptoms, and diabetic retinopathy.

The treatment for the patient in example 3 comprised: daily administration of the daily dose of the Chinese herbal medicine according to the present invention for a period of 7 consecutive days; specifically, a daily dose of Chinese herbal medicine was equally divided for ter in die administration. Particularly, the daily dose of the Chinese herbal medicine in example 3 was the extract of the first mixture; wherein the first mixture additionally included 23 parts by weight of rhizoma Coptidis (*Coptidis Rhizoma*), 18 parts by weight of cortex Mori (*Mori Cortex*), 4 parts by weight of Rhizoma Chuanxiong (*Chuanxiong Rhizoma*), 8 parts by weight of rhizoma Drynariae (*Drynariae Rhizoma*), 4 parts by weight of Radix Salviae Miltiorrhizae (*Salviae Miltiorrhizae Radix* et *Rhizoma*), 4 parts by weight of Fructus Crataegi (*Crataegi Fructus*), 3 parts by weight of Radix Angelicae Sinensis (*Angelicae Sinensis Radix*), 3 parts by weight of Radix Ginseng (*Ginseng Radix* et *Rhizoma*), and 3 parts by weight of Radix Panax notoginseng (*Notoginseng Radix* et *Rhizoma*).

After the 7 days course of treatment (administering daily dose for each day), the outcome of the condition of the diabetes patient included:

GLU(AC) reduced to 120-150 approximately; during the course of treatment, 38 U of insulin is needed for one day. The Chinese herbal medicine of the present invention was able to substitute insulin and achieve the purpose of alleviating diabetic condition as well as abstaining drug dependence without suffering from withdrawal symptoms.

Example 4: Patient 4

The diabetes patient of example 4 was diagnosed to have the condition including GLU(AC):95-185, administering insulin approximately 24 U for one day for years to improve diabetic symptoms.

The treatment for the patient in example 4 comprised: daily administration of the daily dose of the Chinese herbal medicine according to the present invention for a period of 7 consecutive days; specifically, a daily dose of Chinese herbal medicine was equally divided for ter in die administration. Particularly, the daily dose of the Chinese herbal medicine in example 4 was the extract of the first mixture; wherein the first mixture additionally included 25 parts by weight of rhizoma Coptidis (*Coptidis Rhizoma*), 13 parts by weight of cortex Mori (*Mori Cortex*), 12 parts by weight of Phelloendron amurense bark (*Phellodendri Chinensis Cortex*), 8 parts by weight of rhizoma Drynariae (*Drynariae Rhizoma*), 4 parts by weight of Radix Salviae Miltiorrhizae (*Salviae Miltiorrhizae Radix* et Rhizoma), 4 parts by weight of Fructus Crataegi (*Crataegi Fructus*), 3 parts by weight of Rhizoma Chuanxiong (*Chuanxiong Rhizoma*), 3 parts by weight of Radix Ginseng (*Ginseng Radix* et *Rhizoma*), 3 parts by weight of Radix Panax notoginseng (*Notoginseng Radix* et *Rhizoma*), 1 part by weight of Velvet antler, and 5 parts by weight of Radix Puerariae (*Puerariae Lobatae Radix*).

After the 7 days course of treatment (administering daily dose for each day), the outcome of the condition of the diabetes patient included:

GLU(AC) reduced to 101-137 approximately; during the course of treatment, 24 U of insulin is needed for one day. The Chinese herbal medicine of the present invention was able to substitute insulin and achieve the purpose of alleviating diabetic condition as well as abstaining drug dependence without suffering from withdrawal symptoms.

Example 5: Patient 5

The diabetes patient of example 5 was diagnosed to have the condition including GLU(AC): 169-224, administering insulin approximately 27 U for one day for years to improve diabetic symptoms.

The treatment for the patient in example 5 comprised: daily administration of the daily dose of the Chinese herbal medicine according to the present invention for a period of 14 consecutive days; specifically, a daily dose of Chinese herbal medicine was equally divided for ter in die administration. Particularly, the daily dose of the Chinese herbal medicine in example 5 was the extract of the first mixture; wherein the first mixture additionally included 25 parts by weight of rhizoma Coptidis (*Coptidis Rhizoma*), 15 parts by weight of cortex Mori (*Mori Cortex*), 12 parts by weight of Phelloendron amurense bark (*Phellodendri Chinensis Cortex*), 5 parts by weight of rhizoma Drynariae (*Drynariae Rhizoma*), 4 parts by weight of Radix Salviae Miltiorrhizae (*Salviae Miltiorrhizae Radix* et Rhizoma), 4 parts by weight of Rhizoma Chuanxiong (*Chuanxiong Rhizoma*), 3 parts by weight of Radix Ginseng (*Ginseng Radix* et *Rhizoma*), 3 parts by weight of Radix Panax notoginseng (*Notoginseng Radix* et *Rhizoma*), and 1 part by weight of Velvet antler.

After the 14 days course of treatment (administering daily dose for each day), the outcome of the condition of the diabetes patient included:

GLU(AC) reduced to 115-178 approximately; during the course of treatment, lower dose of insulin is needed for one day. The Chinese herbal medicine of the present invention was able to substitute insulin and achieve the purpose of alleviating diabetic condition as well as abstaining drug dependence without suffering from withdrawal symptoms.

Example 6: Patient 6

The diabetes patient of example 6 was diagnosed to have the condition including GLU(AC): 169-224, administering insulin approximately 10 U for one day for years to improve diabetic symptoms.

The treatment for the patient in example 6 comprised: daily administration of the daily dose of the Chinese herbal medicine according to the present invention for a period of 21 consecutive days=; specifically, a daily dose of Chinese herbal medicine was equally divided for ter in die administration. Particularly, the daily dose of the Chinese herbal medicine in example 6 was the extract of the first mixture; wherein the first mixture additionally included 25 parts by weight of rhizoma Coptidis (*Coptidis Rhizoma*), 20 parts by weight of cortex Mori (*Mori Cortex*), 12 parts by weight of Phelloendron amurense bark (*Phellodendri Chinensis Cortex*), 4 parts by weight of Radix Salviae Miltiorrhizae (*Salviae Miltiorrhizae Radix* et *Rhizoma*), 4 parts by weight of Rhizoma Chuanxiong (*Chuanxiong Rhizoma*), 2 parts by weight of salt, 4 parts by weight of Alisma rhizome (*Alismatis Rhizoma*), 8 parts by weight of Radix Dipsaci (*Dipsaci Radix*), 2.5 parts by weight of Herba Ephedrae (*Ephedrae Herba*), 3 part by weight of Pimenta officinalis seed, 3 parts by weight of Radix Ginseng (*Ginseng Radix* et *Rhizoma*), 3 parts by weight of Radix Panax notoginseng (*Notoginseng Radix* et *Rhizoma*), 1 part by weight of Velvet antler.

After the 21 days course of treatment (administering daily dose for each day), the outcome of the condition of the diabetes patient included:

GLU(AC) reduced to 123-182 approximately; during the course of treatment, 6 U of insulin was needed for one day. The Chinese herbal medicine of the present invention was able to substitute insulin and achieve the purpose of alleviating diabetic condition as well as abstaining drug dependence without suffering from withdrawal symptoms.

While the preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents are covered thereby.

What is claimed is:

1. A method of reducing a dosage of insulin for a diabetes subject, comprising administering a therapeutically effective amount of Chinese herbal medicine to a subject in need thereof;
    wherein the Chinese herbal medicine is an extract of a first mixture comprising 4-6 parts by weight of raw oyster shell powder, 4-6 parts by weight of raw Os Draconis, 7-9 parts by weight of Haematitum (Hematite), 2-4 parts by weight of Magnetitum (Magnetite), 4-6 parts by weight of radix Achyranthis Bidentatae (*Achyranthes bidentata*), 4-6 parts by weight of rhizoma Dioscoreae (*Dioscoreae Rhizoma*), 4-6 parts by weight of radix Paeoniae Rubra (*Paeoniae Radix Rubra*), 4-6 parts by weight of radix Rehmanniae (*Rehmannia*), and 3-5 parts by weight of semen Platycladi (*Platycladi Semen*).

2. The method as claimed in claim 1, wherein the Chinese herbal medicine is prepared by following steps:
    providing the first mixture;
    mixing the first mixture and water to form a second mixture;
    heating the second mixture to obtain a crude extract; and
    filtering the crude extract and retaining the liquid, to obtain the Chinese herbal medicine.

3. The method as claimed in claim 1, wherein the part by weight of the first mixture is 3.75 gram per part.

4. The method as claimed in claim 1, wherein the first mixture further comprises, Radix Ginseng (*Ginseng Radix et Rhizoma*), Radix Panax notoginseng (*Notoginseng Radix et Rhizoma*), 5-25 parts by weight of rhizoma Coptidis (*Coptidis Rhizoma*), 5-20 parts by weight of cortex Mori (*Mori Cortex*), 7-9 parts by weight of rhizoma Drynariae (*Drynariae Rhizoma*), 3-5 parts by weight of Rhizoma Chuanxiong (*Chuanxiong Rhizoma*), 3-5 parts by weight of Radix Salviae Miltiorrhizae (*Salviae Miltiorrhizae Radix et Rhizoma*), 3-5 parts by weight of Fructus Crataegi (*Crataegi Fructus*), 2-4 parts by weight of Radix Angelicae Sinensis (*Angelicae Sinensis Radix*), 4-6 parts by weight of Radix Puerariae (*Puerariae Lobatae Radix*), 10-17 parts by weight of Phelloendron amurense bark (*Phellodendri Chinensis Cortex*), 8-12 parts by weight of gypsum powder, 3-5 parts by weight of rhizoma Gastrodiae (*Gastrodiae Rhizoma*), 3-5 parts by weight of Radix asparagi (*Asparagi Radix*), 7-9 parts by weight of Radix Dipsaci (*Dipsaci Radix*), 0-3 parts by weight of salt, 2-4 parts by weight of Pimenta officinalis seed, 2-4 parts by weight of Atractylodes Lancea Rhizoma (*Atractylodis Rhizoma*), 0-3 parts by weight of velvet antler, 4-6 parts by weight of Alisma rhizome (*Alismatis Rhizoma*), 0-3 parts by weight of Herba Ephedrae (*Ephedrae Herba*), or the combination thereof.

5. The method as claimed in claim 1, wherein the method further comprises administering a therapeutically effective amount of insulin to a subject in need thereof.

6. The method as claimed in claim 1, wherein the diabetes subject is being treated for insulin resistant diabetes mellitus which is a treatment for hyperglycemia.

7. The method as claimed in claim 1, wherein the diabetes is familial hereditary diabetes.

8. The method as claimed in claim 1, wherein the extract or powder of the Chinese herbal medicine is administered via oral administration, enteral administration, or intravenous injection.

9. The method as claimed in claim 1, wherein the Chinese herbal medicine further comprises a pharmaceutically acceptable carrier, stabilizer, diluent, dispersant, suspending agents, thickening agent, or excipient, or a combination thereof.

* * * * *